US006426426B1

(12) United States Patent
Ferrer et al.

(10) Patent No.: US 6,426,426 B1
(45) Date of Patent: Jul. 30, 2002

(54) PROCEDURE FOR THE PREPARATION OF AROMATIC DERIVATIVES OF TITANOCENE

(75) Inventors: Maria Dolores Parellada Ferrer; Juan Antonio Barrio Calle; José Sancho Royo; Luis Mendez Llatas, all of Madrid (ES)

(73) Assignee: Repsol Quimica, S.A., Madrid (ES)

( * ) Notice: Subject to any disclaimer, the term of this patent is extended or adjusted under 35 U.S.C. 154(b) by 0 days.

(21) Appl. No.: 09/673,228

(22) PCT Filed: Apr. 15, 1998

(86) PCT No.: PCT/ES98/00094

§ 371 (c)(1),
(2), (4) Date: Oct. 11, 2000

(87) PCT Pub. No.: WO99/52918

PCT Pub. Date: Oct. 21, 1999

(51) Int. Cl.$^7$ .............................. C07F 7/28; C07F 17/00
(52) U.S. Cl. ........................ 556/53; 526/160; 526/943; 502/103; 502/117
(58) Field of Search .......................... 556/53; 502/103, 502/117; 526/160, 943

(56) References Cited

U.S. PATENT DOCUMENTS

| 2,952,670 A |   | 9/1960 | Fischer ...................... 260/93.5 |
| 3,000,870 A |   | 11/1961 | Pino et al. .................. 260/93.5 |
| 5,892,082 A | * | 4/1999 | Cai et al. ....................... 556/53 |
| 6,175,025 B1 | * | 1/2001 | Kitagawa et al. .............. 556/22 |

FOREIGN PATENT DOCUMENTS

| EP | 0 601 953 B1 | 5/1997 |
| JP | 57-11989 | 1/1982 |
| NL | 6603202 | 3/1966 |
| WO | WO 97/09336 | 3/1997 |

OTHER PUBLICATIONS

Natta, G., et al. "Lettere Alla Direzione: Polimerizzazione dell' etilene catalizzata da composti di titanio," *La Chimica e l'Industria*, vol. 12, pp. 1032–1033 (1957).
Ryabov, A.V. et al., "Vysokomol. Soekin," *Ser. Bll*, pp. 49–52 (1969).
Herman, Daniel F., et al., "Isolation of a Compound Containing the Covalent Titanium–Carbon Bond," *Journal Amer. Chem. Soc.*, vol. 74, p. 2693 (1952).
Summers, L., et al., "Reaction of Bis–(cyclopentadienyl) –titanium Dichloride with Aryllithium Compounds," *Journal Amer. Chem. Soc.*, vol. 76, pp. 2278–2279 (1954).
Summers, L., et al., "Diaryl Bis–(cyclopentadienyl) –titanium Compounds," *Journal Amer. Chem. Soc.*, vol. 77, pp. 3604–3606, (1955).
Beachell, H.C., and Butter, S.A., "Nuclear Magnetic Resonance Spectra a Titanocene Sandwich Compounds," *Inorganic Chemistry*, vol. 4, No. 8, pp. 1133–1140 (1965).
Liu, et al., *J. Huaxue Tongbao*, vol. 10, p. 26, (1984).

* cited by examiner

*Primary Examiner*—Porfirio Nazario-Gonzalez
(74) *Attorney, Agent, or Firm*—Ladas & Parry

(57) ABSTRACT

Procedure for the preparation of aromatic derivatives of titanocene, useful as catalysts for the polymerisation and hydrogenation of polymers, characterised by the use of a Grignard reagent. This procedure allows to easily prepare compounds with the general formula (I)

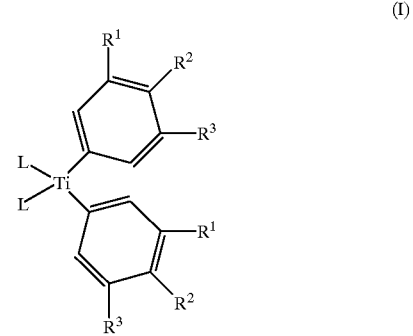

where:
L, which can be equal to or different one from the other, are cyclopentadiene, or pentamethylcyclopentadiene; preferably at least one L is cyclopentadiene; $R^1$, $R^2$, $R^3$, equal or different from one another, are selected from the group consisting of: hydrogen, alkyl group from 1 to 4 carbon atoms, $OR^4$ where $R^4$ is an alkyl group of 1 to 4 carbon atoms; at least one of the $R^1$, $R^2$ or $R^3$ is hydrogen. The preparation is carried out by the reaction of the titanocene dichloride with the corresponding Grignard reagent. This method substantially enhances safety, reproducibility, yield and cost of that carried out via lithium compounds.

15 Claims, No Drawings

PROCEDURE FOR THE PREPARATION OF AROMATIC DERIVATIVES OF TITANOCENE

This invention refers to a procedure for the preparation of aromatic compounds of titanocene. More particularly it refers to a procedure of synthesis of bis(aryl) and bis(cyclopentadienyl) titanium derivatives via the Grignard reagent.

State of the Art

The alkyl and aryl compounds derived from titanocene are very useful in numerous organic reactions, for instance as catalysts for the polymerisation and hydrogenation of polymers. The large number of publications (U.S. Pat. No. 2,952,670 (1960); Gevaert-Agfa, Neth. Patent 6,603,202 (1966); Natta, G., et al, Chim. Ind. (Milan) 39, 1032 (1957); U.S. patent application Ser. No. 3,000,870 (1958); Ryabov, A. V., et al., Vysokomol. Soedin, Ser. Bll, 49 (1969)), evidences the interest aroused by bis(cyclopentadienyl) bis (phenyl) titanium as catalyst together with titanium tetrachloride or an alkyl aluminium compound for the polymerisation of ethylene.

On the other hand, the hydrogenation catalyst activity of polymers of bis(cyclopentadienyl) bis(alkylphenil)titanium described in patent GB 2159819 or bis (cyclopentadienyl) bis(alcoxyphenyl) titanium claimed in patent EP 0 601 953 is well known.

The efforts to prepare organotitanium compounds with σ bonds date back to more than a century ago, but it was not until 1952 that Herman et al., J. Amer., Chem. Soc. 74,2693 (1952) synthesised the first organotitanium compound. Somewhat latter, in 1954 the first bis(aryl) derivatives of bis(cyclopentadienyl) titanium were isolated by reaction of titanocene dichloride and the corresponding aryl lithium salt, being in this way that L. Summers et al, (J. Amer., Soc. 76, 2278 (1954) and J. Amer., Chem. Soc., 77,3604 (1955)) prepared phenyl, 3-tolyl, 4-tolyl and 4-dimethylaminephenyl derivatives with yields above 81%. Subsequently Beachell and Butter (Inorg. Chem, 4,1133 1965) described the synthesis of the $Cp_2Ti(3-CF_3C_6H_4)_2$ and $CP_2Ti(4-XC_6H_4)_2$ derivatives where $X=OCH_3$, F, Cl, Br, $CF_3$) using the same synthesis path. The preparation of diaryl titanocene derivatives by reaction with aryl lithium was again published by Liu et al. in J. Huaxue Tongbao, 10, 26, (1984).

The use of lithium compounds involves the use of very volatile solvents, very low temperatures (−70° C.), extremely humidity sensitive reactants and pyrophoric products, which implies an important risk and complexity in the preparation of diaryl titanocene derivatives at industrial scale.

On our side, we have discovered that, surprisingly, the bis(aryl) derivatives of titanocene can be easily prepared by the reaction of titanocene dichloride with the corresponding Grignard derivative. This method substantially enhances safety, reproducibility, yield and cost of the method which is carried out via lithium compounds.

Description of the Invention

The procedure of this invention is characterised by the use of an organo magnesium for the manufacturing of compounds which have the following formula:

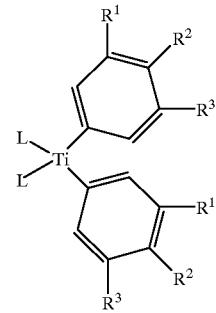

(I)

where:
L, which can be equal or different one from the other, are cyclopentadiene, or pentamethylcyclopentadiene; preferably at least one L is cyclopentadiene; $R^1$, $R^2$, $R^3$, are equal or different from one another, are selected from a group consisting of: hydrogen, alkyl group of 1 to 4 carbon atoms, OR4 where R4 is an alkyl group of 1 to 4 carbon atoms; at least one of the $R^1$, R2 or $R^3$ is hydrogen.

The procedure for the preparation of said titanocenes is characterised by the following steps:

Preparation of the Grignard reagent by reaction of magnesium metal with a compound with the formula (II):

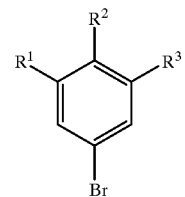

(II)

$BrC_6H_4R$, where $R^1$, $R^2$ and $R^3$ have already been defined and Br is bromide, in a polar solvent such as tetrahydrofuran;

b) Reaction of the Grignard reagent in solution with titanocene dichloride in a 2:1 ratio;

Precipitation with a non-polar solvent, such as cyclohexane, of the chlorobromomagnesium salts synthesised in the reaction medium and filtration of the same, obtaining a solution of the compound (I).

Preferably the process according to the following invention refers to compounds which have the formula III

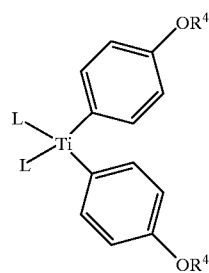

where:
L, which can be equal or different one from the other, are cyclopentadiene, or pentamethylcyclopentadiene; preferably at least one L is cyclopentadiene; OR4 is an alcoxyle group, containing from 1 to 4 carbon atoms.

The advantages posed by this method respect of those described in the preceding state of art, are the use of less volatile solvents, reaction temperatures between 0 and 70° C., cheaper and not so humidity sensitive reactants, which makes operation more simple and safe, and easy to be carried out at an industrial scale. Preferably the solvents used are liquid with boiling points higher than or equal to 65° C.

Specific examples of the compounds prepared are: bis(4-methoxyphenyl) bis(cyclopentadienyl) titanium, bis(3-methoxyphenyl) bis(cyclopentadienyl) titanium, bis(4-etoxyphenyl) bis(cyclopentadienyl) titanium, bis(3-etoxyphenyl) bis(cyclopentadienyl) titanium, bis(4-methylphenyl) bis(cyclopentadienyl) titanium, bis(phenyl) bis(cyclopentadienyl) titanium, bis(4-ethylphenyl) bis(cyclopentadienyl) titanium, bis(3-ethylphenyl) bis(cyclopentadienyl) titanium, bis(4-butylphenyl) bis(cyclopentadienyl) titanium, bis(3-butylphenyl) bis(cyclopentadienyl) titanium, bis(3-ethyl,4-methylphenyl) bis(cyclopentadienyl) titanium, bis(4-methoxyphenyl) (cyclopentadienyl) (pentamethylcyclopentadienyl) titanium, bis(3-methoxyphenyl) (cyclopentadienyl) (pentamethylcyclopentadienyl) titanium, bis(4-etoxyphenyl) (cyclopentadienyl) (pentamethylcyclopentadienyl) titanium, bis(3-etoxyphenyl) (cyclopentadienyl) (pentamethylcyclopentadienyl) titanium, bis(4-methylphenyl) (cyclopentadienyl) (pentamethylcyclopentadienyl) titanium, bis(phenyl) (cyclopentadienyl) (pentamethylcyclopentadienyl) titanium, bis(4-ethylphenyl) (cyclopentadienyl) (pentamethylcyclopentadienyl) titanium, bis(3-ethylphenyl) (cyclopentadienyl) (pentamethylcyclopentadienyl) titanium, bis(4-butylphenyl) (cyclopentadienyl) (pentamethylcyclopentadienyl) titanium, bis(3-butylphenyl) (cyclopentadienyl) (pentamethylcyclopentadienyl) titanium, bis(3-ethyl,4-methylphenyl) (cyclopentadienyl) (pentamethylcyclopentadienyl) titanium, bis(4-methoxyphenyl) bis(pentamethylcyclopentamethyl) titanium, bis(3-methoxyphenyl) bis(pentamethylcyclopentamethyl) titanium, bis(4-ethoxyphenyl) bis(pentamethylcyclopentamethyl) titanium, bis(3-ethoxyphenyl) bis(pentamethylcyclopentamethyl) titanium, bis(4-methylphenyl) bis(pentamethylcyclopentamethyl) titanium, bis (phenyl) bis(pentamethylcyclopentamethyl) titanium, bis(4-ethylphenyl) bis(pentamethylcyclopentamethyl) titanium, bis(3-ethylphenyl) bis(pentamethylcyclopentamethyl) titanium, bis(4-ethylphenyl) bis(pentamethylcyclopentamethyl) titanium, bis(3-butylphenyl) bis(pentamethylcyclopentamethyl) titanium, bis(3-ethyl,4-methylphenyl) bis(pentamethylcyclopentamethyl) titanium.

The products prepared by the method described in this invention are obtained with quantitative yields and with a purity of >97%.

An additional advantage of this procedure is that the titanocene derivative is obtained in solution at an adequate concentration for its direct use in polymerisation or hydrogenation reactions. The solutions of bis(aryl) derivatives are stable at room temperature for long periods of time.

In the procedure described in this invention the reaction with the titanocene dichloride is carried out in the same reactor in which the intermediate Grignard derivative has been synthesised, not being necessary to isolate it, which simplifies and eases the operation.

Below are some explanatory examples of the procedure subject matter of the invention which evidence the advantages of the method compared to those described in the preceding state of art. These examples are not intended as limitations of the invention:

EXAMPLE

Example 1

Preparation of the bis(4-methoxyphenyl) bis(cyclopentadienyl) titanium

The preparation is carried out in a 25 L reactor, lined and with a mechanical shaker, which is connected to a reflux condenser. The reactions are carried out at atmospheric pressure and inert conditions.

The reactor is loaded with 195 gr (7,99 mol) of magnesium chips and 9 L of dry tetrahydrofuran, initiating the heating through the lining. When the inside temperature of the reactor reaches 65° C. a portion of 4-bromoanysol is added. After a few minutes, a vigorous reflux is noted, which indicates the initiation of the reaction. The rest of 4-bromoanysol (1500 gr total, 8.04 mol) is added in small portions, maintaining a constant reflux. Once the adding is finished, the temperature is kept constant at 65° C. for 2 h. longer.

The reaction mixture is cooled at a temperature below 10° C. and the solid titanocene dichloride is added in portions (995 gr., 3.99 mol total), controlling that the temperature of the reactor does not exceed 25° C.

After 1 more hour refrigerating, 9 L of cyclohexane are added and the reaction mixture is shaken and left to cool off to facilitate the precipitation of chlorobromomagnesium salts. It is pressure filtered and the filtrate is stored in inert conditions. The quality of the solution obtained is assayed by UV-Visible spectrophotometry and by 1H-NMR. Quantitative yield is obtained, 1.6 Kg of product in solution.

Example 2(Comparative)

This example corresponds to the synthesis of bis(4-methoxyphenyl) bis(cyclopentadienyl) titanium prepared according to the preceding state of art.

The preparation is carried out by reaction of titanocene dichloride with a 4-methoxyphenyl lithium derivative. The reactions are carried out in a schlenk, a glass apparatus which allows the carrying out of different operations: transfer, filtration, vacuum elimination of the solvent . . . , etc. in inert atmosphere conditions.

In a schlenk of 1 L conditioned with Argon 49.15 g. (0.21 mol) of 4-iodine anysol are weighed and 300 ml of dry ethyl ether are added. This solution is cooled at −78° C. and the stoichiometric amount of n-butyl lithium is added (13.45 g, 0.21 mol). After adding it the reaction mixture is allowed to slowly reach room temperature, completing the reaction and obtaining the lithium derivative in solution. This product in the solid state is highly pyrophoric, so that precautions must be taken in order that no solid deposits are formed by evaporation of the solvent.

To the lithium derivative solution cooled at 0° C., 24.9 g (0.10 mol) of titanocene dichloride in dry ethyl ether suspension are added. After the adding the reaction is allowed to reach room temperature and is shaken for to 2 h. longer. The reaction mixture is filtered and the lithium chloride is washed with ethyl ether. The solution and the washings are vacuum dried, obtaining the product as an oily solid, which can be recrystallised with petroleum ether. The solid product is reddish orange with a tendency to become oily at room temperature. The yield with this type of synthesis is about 90%.

What is claimed is:

1. A procedure for obtaining a titanocene compound having a formula (I):

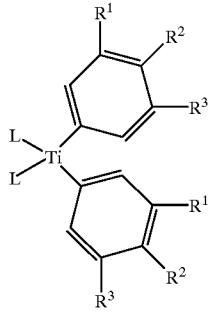

(I)

where:

each L is independently cyclopentadiene or pentamethylcyclopentadiene; $R^1$, $R^2$, and $R^3$ are equal to or different from each other and are selected from the group consisting of: hydrogen, an alkyl group of 1 to 4 carbon atoms, and $OR^4$, where $R^4$ is an alkyl group of 1 to 4 carbon atoms; at least one of $R^1$, $R^2$, and $R^3$ is hydrogen; the procedure comprising the following steps:

(a) preparation of a Grignard reagent by reaction in a polar solvent of magnesium metal with a compound having a formula (II):

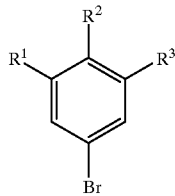

(II)

where $R^1$, $R^2$, and $R^3$ have already been defined and Br is bromine;

(b) reaction of the Grignard reagent in solution with titanocene dichloride in a 2:1 ratio to yield a reaction medium;

(c) precipitation with a non-polar solvent of chlorobromomagnesium salts that are generated in the reaction medium and filtration of the reaction medium to obtain a solution of the compound having the formula (I).

2. A procedure according to claim 1 wherein at least one L is cyclopentadiene.

3. A procedure according to claim 1 where the titanocene compound has a formula (III):

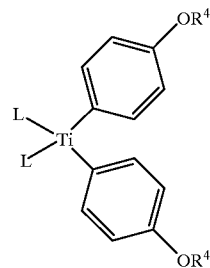

where:
each L is independently cyclopentadienyl or pentamethylcyclopentadienyl; and $OR^4$ is an alkoxy group containing from 1 to 4 carbon atoms.

4. A procedure according to claim 1, wherein the solvent used in step (a) comprises a liquid with a boiling point greater than or equal to 65°C.

5. A procedure according to claim 1, wherein the solvent used in step (a) comprises tetrahydrofuran.

6. A procedure according to claim 1, where the compound having the formula (I) is bis(4-methoxy phenyl) bis (cyclopentadienyl) titanium.

7. A procedure according to claim 2 where the titanocene compound has a formula (III):

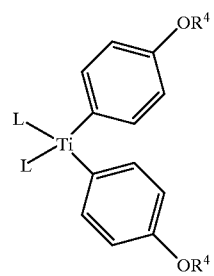

where:
each L is independently cyclopentadienyl or pentamethylcyclopentadienyl; and $OR^4$ is an alkoxy group containing from 1 to 4 carbon atoms.

8. A procedure according to claim 2, wherein the solvent used in step (a) comprises a liquid with a boiling point greater than or equal to 65° C.

9. A procedure according to claim 3, wherein the solvent used in step (a) comprises a liquid with a boiling point greater than or equal to 65° C.

10. A procedure according to claim 2, wherein the solvent used in step (a) comprises tetrahydrofuran.

11. A procedure according to claim 3, wherein the solvent used in step (a) comprises tetrahydrofuran.

12. A procedure according to claim 4, wherein the solvent used in step (a) comprises tetrahydrofuran.

13. A procedure according to claim 2, where the compound having the formula (I) is bis(4-methoxy phenyl) bis(cyclopentadienyl) titanium.

14. A procedure according to claim 3, where the compound having the formula (I) is bis(4-methoxy phenyl) bis(cyclopentadienyl) titanium.

15. A procedure according to claim 4, where the compound having the formula (I) is bis(4-methoxy phenyl) bis(cyclopentadienyl) titanium.

* * * * *